(12) United States Patent
Veelenturf et al.

(10) Patent No.: US 6,241,950 B1
(45) Date of Patent: Jun. 5, 2001

(54) FLUID SAMPLING SYSTEM

(75) Inventors: Robert Veelenturf, Norfolk; David W. Bearg, Concord, both of MA (US)

(73) Assignee: Airxpert Systems, Inc., Lexington, MA (US)

( * ) Notice: Subject to any disclaimer, the term of this patent is extended or adjusted under 35 U.S.C. 154(b) by 0 days.

(21) Appl. No.: 09/023,846

(22) Filed: Feb. 13, 1998

(51) Int. Cl.[7] ...................................................... B01L 11/00
(52) U.S. Cl. .................... 422/103; 422/68.1; 422/82.13; 422/83; 422/93; 422/100; 422/82.12; 73/863.31; 73/863.33; 73/863.86; 73/863.71
(58) Field of Search ................................ 422/68.1, 82.13, 422/93, 83, 100; 436/171; 73/863.31, 863.33, 863.86, 863.71

(56) References Cited

U.S. PATENT DOCUMENTS

| | | | |
|---|---|---|---|
| 3,474,656 | * 10/1969 | Kelleher | 73/23.1 |
| 3,685,355 | 8/1972 | DeBaun | 73/212 |
| 3,757,583 | * 9/1973 | Ludewig, Jr. | 73/421.5 R |
| 3,842,677 | * 10/1974 | Bufkin et al. | 73/421.5 R |
| 3,900,290 | * 8/1975 | Hornstra | 23/230 B |
| 4,046,012 | * 9/1977 | Studenick | 73/421.5 R |
| 4,090,392 | * 5/1978 | Smith et al. | 73/421.5 R |
| 4,263,931 | 4/1981 | Bramow et al. | 137/84 |
| 4,297,900 | * 11/1981 | Brandt, Jr. | 73/861.66 |
| 4,414,858 | * 11/1983 | Peterson et al. | 73/863.33 |
| 4,594,888 | 6/1986 | DeBaun et al. | 73/198 |
| 4,859,419 | * 8/1989 | Marks et al. | 422/56 |
| 4,947,339 | * 8/1990 | Czekajewski et al. | 364/497 |
| 5,233,876 | * 8/1993 | LaPack et al. | 73/863.23 |
| 5,292,280 | 3/1994 | Janu et al. | 454/229 |
| 5,469,751 | * 11/1995 | Weiss et al. | 73/863.33 |
| 5,922,286 | * 7/1999 | Girard et al. | 422/83 |

FOREIGN PATENT DOCUMENTS 2077376   8/1992   (CA) .......................... G01N/001/26

OTHER PUBLICATIONS

Bruel & Kjaer, Product Data brochures, Multipoint Sampler and Doser—Type 1303, Optical Filters, Thermal Environment Measuring Equipment, Application Software, Multi-gas Monitor—Type 1302 (undated product brochure available before Feb. 13, 1998).

Johnson Controls, Metasys Compatible Products, 7/96.

Johnson Controls, The Metasys Ventilation Control Application (undated product brochure available before Feb. 13, 1998).

Solomat, IAQ Surveyor Indoor Air Quality Monitoring, Zellweger Analytics (undated product brochure available before Feb. 13, 1998).

TeleSense Corporation, Three Ways to Improve Your Safety in the Fab (undated product brochure available before Feb. 13, 1998).

Yokogawa, Halogen Gas Monitor, 1993.

Yokogawa, Refrigerant Gas Monitoring System, 1994.

* cited by examiner

*Primary Examiner*—Jill Warden
*Assistant Examiner*—Kathryn Bex
(74) *Attorney, Agent, or Firm*—Fish & Richardson P.C.

(57) ABSTRACT

A fluid sampling device including a manifold having inputs, common purge and sampling pathways, valves disposed to couple and decouple a first set of the inputs to the common purge pathway and a second set of the inputs to the common sampling pathway, and a differential sensor coupled to the pathways. A controller connected to the valves produces control signals that enable the valves to couple and decouple the inputs to the common sensor and purge pathways. In addition, a method for operating a fluid sampling system that is connected to a set of sample zones that includes the steps of sampling fluid from first and second sample zones in respective first and second sample locations, isolating third and fourth sample zones from the first and second sample locations, and measuring a differential parameter across the sample locations.

42 Claims, 8 Drawing Sheets

FLUID SAMPLING SYSTEM

BACKGROUND OF THE INVENTION

This invention relates to systems that measure parameters of a fluid.

The sampling of fluid within a system allows the fluid to be tested for concentration of various substances. Typically, the fluid within an environmental system such as the air in an office building or a hospital is monitored to determine the level of pollutants such as carbon monoxide and carbon dioxide in the system. The information obtained during the monitoring can be used to control a heating ventilation and air conditioning (HVAC) system, e.g., to control indoor air quality (IAQ). In one approach to monitoring IAQ, remote sampling systems are connected to various locations in the system by a network of tubes that shunt fluid to a central location where in-line measurements are made on air components. In other monitoring systems, sensors are distributed throughout a building and electronically communicate with a central controller.

In addition to monitoring the level of pollutants, it is desirable to monitor and control the flow of pollutants such as carbon monoxide (CO), carbon dioxide ($CO_2$), odors, and dust by monitoring and controlling the fluid flow within the system. Thus, the pressure within the system, especially the pressure differential between two locations within the system, often is measured to determine fluid flow within the system. For example, pressure differentials across the external walls of a building are important to maintain a positive indoor pressure, especially at the lower levels of a building where negative pressures are more likely to form due to the buoyant force of heated air. The positive indoor pressure prevents air from entering the building as a draft and forces outdoor air to be introduced through the HVAC system where it is conditioned properly and filtered. Because pressure differentials within a building dictate the flow of air, they are important in the control of contaminants in sterile environments as in hospitals. In addition, pressure differentials across the wall of an air duct can be used to determine volumetric airflow within a component of an environmental system.

A typical method for measuring pressure includes connecting pressure sensors to various locations within the system and comparing the pressure measurements to determine the magnitude and direction of fluid flow. A set of sensors may be used at each location with each sensor being most accurate in a different range.

SUMMARY OF THE INVENTION

One aspect of the invention is a fluid sampling device that includes a manifold having a plurality of inputs, a common purge pathway, a common sampling pathway, a plurality of valves to couple and decouple some inputs to the common purge pathway and other inputs to the common sampling pathway. The system also includes a differential pressure sensor coupled to the common sampling pathways.

Preferred embodiments of this aspect include the following features.

A controller connected to the plurality of valves produces control signals that enable the valves to couple and decouple the inputs to the common pathways. The controller produces control signals to configure the valves such that one of the valves couples an input to the common sensor pathway, another one of the valves couples a different input to the common purge pathway, and a set of valves decouples the common pathways from other inputs. The controller produces control signals to cause the differential pressure sensor to measure differential pressure across the common pathways. The differential pressure sensor either is two individual sensors coupled to one each of the common pathways, or is a plurality of sensors that measures pressure in different pressure ranges. The controller causes the pressure sensors to each measure differential pressure across the common sampling pathway and the common purge pathway to provide indications, e.g., an electronic or other signal, of the differential pressure between the input ports.

In another aspect of the invention, a manifold has multiple input ports, at least two common output ports, and a set of valve pairs. Each pair of valves corresponds to an input port. One of the valves of the pair couples and decouples the input port to one output port, and the other valve of the pair couples and decouples the input port to the other output port. A differential pressure sensor is coupled between the two output ports.

In another aspect of the invention, a manifold has two common pathways and at least one input port. The manifold has a plurality of passages, and the input port is in fluid communication with one common pathway through one of the passages. A valve is disposed along the passage and is capable of blocking the flow of fluid between the input port and the common pathway. A pressure sensor is disposed across the sensor pathway and the purge pathway.

Preferred embodiments of this aspect of the invention include the following features.

A second valve is disposed along another passage and is capable of blocking the flow of fluid between the input port and the second common pathway. Another input port is in fluid communication with one of the common pathways through a third passage and is in fluid communication with the other common pathway through a fourth passage. Third and fourth valves are disposed along the third and fourth passages respectively. Both valves are capable of blocking the flow of fluid between the second input port and one of the common pathways. A controller is connected to the first, second, third and fourth valves, and can configure the valves such that the first valve couples the first input port to the first common pathway, the fourth valve couples the second input port to the second common pathway, the second valve decouples the first input port from the second common pathway, and the third valve decouples the second input port from the first common pathway. In an alternate arrangement, the controller can configure the valves such that the second valve couples the first input port to the second common pathway, the third valve couples the second input port to the first common pathway, the first valve decouples the first input port from the first common pathway and the fourth valve decouples the second input port from the second common pathway.

In another aspect of the invention, a manifold has at least two output pathways and at least two input ports. One input port is in fluid communication with one output pathway through one passage of a plurality of passages, and another input port is in fluid communication with another output pathway through another of the passages. A valve of a plurality of valves is disposed along each passage and has a coupled and a decoupled position. A differential pressure sensor is disposed across the output pathways. A sample tube establishes fluid communication between a sample zone and one of the input ports. A sensor is connected to one of the output pathways, and a system controller operates the system.

In another aspect of the invention, a method for measuring differential pressure in a fluid sampling system includes three steps. First, fluid is sampled from a sample zone, through a manifold. The manifold has at least two inputs, at least two outputs, and a plurality of passageways. The inputs are in fluid communication with at least one output through a passageway. A set of valves are disposed along the passageways and have coupled and decoupled positions. Second, the valves are opened such that an output is in fluid communication with a sample zone and another output is in fluid communication with another sample zone. Third, the pressure difference across the two coupled outputs are measured.

Preferred embodiments of this aspect of the invention include the following features.

The pressure difference across the outputs is measured with a plurality of pressure sensors. The pressure difference is processed based both on the value of the sensor indications and on a plurality of pressure ranges that correspond to the pressure sensors.

In another aspect of the invention, a method for operating a fluid sampling system that is connected to a set of sample zones includes two steps. First, fluid from two sample zones is sampled in two sample locations. Second, a differential parameter is measured across the two sample locations. Additionally, two other sample zones can be isolated from the two sample locations.

In another aspect of the invention, a manifold has a plurality of input ports, at least two output ports, and a plurality of paired valves. Each pair of valves corresponds to an input port, one valve of each pair couples and decouples the input port to an output port, the other valve of the pair couples and decouples the input port to the second output port.

In another aspect of the invention, a manifold has at least two output pathways, at least two input ports, and a plurality of passages. An input port is in fluid communication with an output pathway through one of the passages. Another input port is in fluid communication with a second output pathway through a different passage. A plurality of valves, which couple and a decouple an input port from an output pathway, are disposed along the passage connecting the input port and the output pathway.

Preferred embodiments of this aspect of the invention include the following features.

The manifold has at least two common branches. The first common branch connects two input ports to an output pathway; another common branch connects the two input ports to another output pathway.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and not intended to be limiting.

Among other advantages, a differential parameter can be measured at a central location by a single sensor or set of sensors. A fluid can be sampled from any sample zone at a central location in multiple combinations selected by the controller. The system can sample fluid efficiently from a large number of sample zones.

Other features and advantages of the invention will be apparent from the following detailed description, and from the claims.

DETAILED DESCRIPTION OF THE PREFERRED EMBODIMENTS

Figure 1:
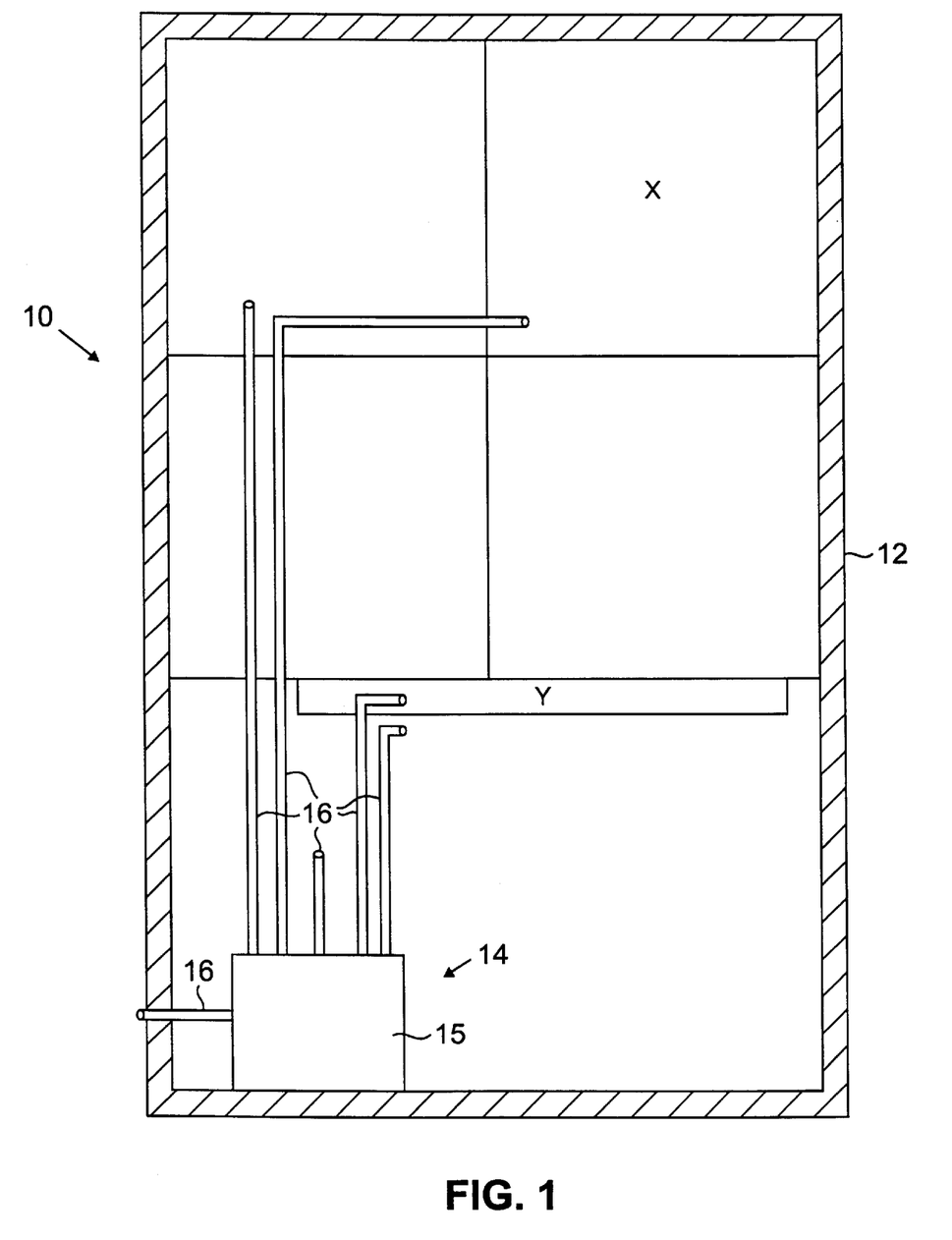
FIG. 1 is a cross-sectional view of a building containing a fluid sampling system.

Referring to FIG. 1, an open environmental system 10, includes an office building 12, and a fluid sampling system 14. The fluid sampling system 14 samples a fluid, e.g. air, that is within the system 10, such as in rooms, air ducts, and reference areas, and air that is outside the system 10 such as outdoor air. The fluid sampling system 14 includes sampling tubes 16 that are connected at a central location to the remote sampling system 14. The tubes are constructed of a plastic material and have an internal diameter that is selected to provide sufficient airflow to the sensors and a resistance tolerable by the vacuum source. For example, the sampling tubes 16 are constructed of, e.g., Plexco®, a black fire retardant plastic material manufactured by Chevron, and have an inner diameter of ⅛". The sampling tubes 16 couple fluid samples from sample zones, e.g., room x or air duct y, to the sampling area 15 where a fluid sample is processed.

Figure 2:
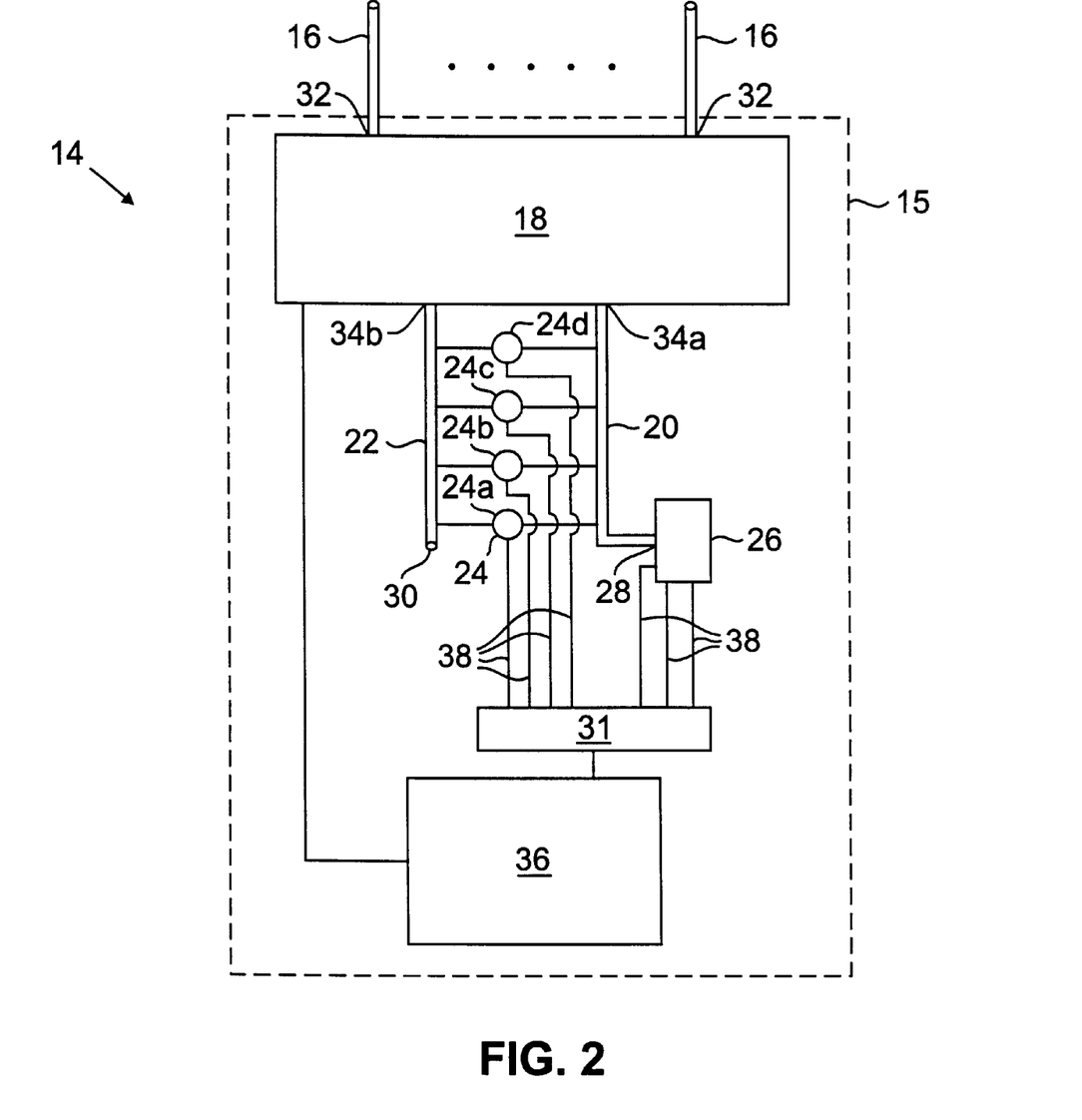
FIG. 2 is a block diagram representation of the fluid sampling system of FIG. 1.

Referring to FIG. 2, the fluid sampling system 14 processes the samples by drawing air from the sample zone through the sample tubes 16 and into a manifold 18 within sampling area 15. The manifold 18 funnels the air into a sensor line 20 and/or a purge line 22. In one mode of operation, the fluid sampling system 14 measures differential parameters. A differential sensor bank 24 is used to measure a differential value of a parameter between the sensor line 20 and purge line 22. The bank of differential sensors 24 is shown coupled across sensor line 20 and purge line 22. A pressure differential measurement is made across the sensor and purge lines 20, 22 using the differential sensor bank 24. The sensor bank 24 includes four individual differential pressure sensors 24a, 24b, 24c, 24d.

In another mode of operation, the fluid sampling system 14 measures singular parameters. The sensor line 20 shunts the air sample to an in-line sensor mechanism 26 where sensor readings are taken and then out of the fluid sampling system 14 via exhaust port 28. Alternatively, the fluid sample is funneled to a purge line 22 and is exhausted from the fluid sampling system 14 via exhaust port 30. The purge line 22 exhausts larger volumes of fluid from the system 14 to purge the system 14 of stale (i.e., outdated) samples to ensure that only fresh (i.e., current) samples are shunted through the sensor line 20 to the sensor mechanism 26. This arrangement would be used to measure values of a parameter at a single sample location rather than a differential parameter between two locations. Parameters that can be measured include concentrations of various substances in the air sample such as, e.g., carbon dioxide and carbon monoxide, and other related measurements such as, e.g., dew point and temperature. In addition, this arrangement of sensor and purge lines 20 and 22 allows a sample line 16 to be flushed simultaneously while a measurement is taken in the sensor line 20 and, thus, increases the sampling rate of the system 14.

The manifold 18 contains a set of input ports 32 and two output ports 34a, 34b. Typically, the manifold could have any number of input ports 32, e.g., 12 or 24 input ports. The sample tubes 16 are connected to the input ports 32 such that, e.g., one sample zone would be in fluid communication with one input port. The sensor and purge lines 20 and 22 are connected respectively to the output ports 34a and 34b. A bank 24 of pressure sensors are shown disposed across the sensor and the purge lines 20, 22. This arrangement allows the system 14 to measure differential pressure between two selected sample zones. The pressure sensors 24a, 24b, 24c, and 24d are coupled across the sensor and purge lines 20, 22. Each of the sensors 24a, 24b, 24c, 24d is designed to measure pressure accurately in different pressure ranges, e.g., four sensors measure the differential pressure with the first sensor 24a accurate in the narrowest range, the second sensor 24b accurate in a broader range, the third sensor 24c accurate in an even broader range, and the fourth sensor 24d accurate in the broadest range. The pressure ranges overlap to allow for more accurate measurements in the narrower ranges. For example, a pressure difference between two rooms is likely to be only 0.051" $H_2O$. A narrower range sensor will give a more accurate reading than a broader range sensor with the same accuracy, e.g., 2%.

Alternatively, the individual sensors 24a, 24b, 24c, 24d can transmit a positive indication rather than a measurement when the pressure falls within the given range of the individual sensor 24.

The fluid sample system 14 is operated by a system controller 36 that controls the flow of air, the selection of sample zones, the measurements, and the data processing. The system controller 36 is, e.g., a microprocessor that is connected to the manifold 18 and the sensors via control signal lines 38. The system controller 36 transmits signals to and/or receives signals from the manifold 18 and the sensors 24, 26. The system controller 36 controls the system according to a software algorithm customized to the attributes of the system 14.

Figure 3:
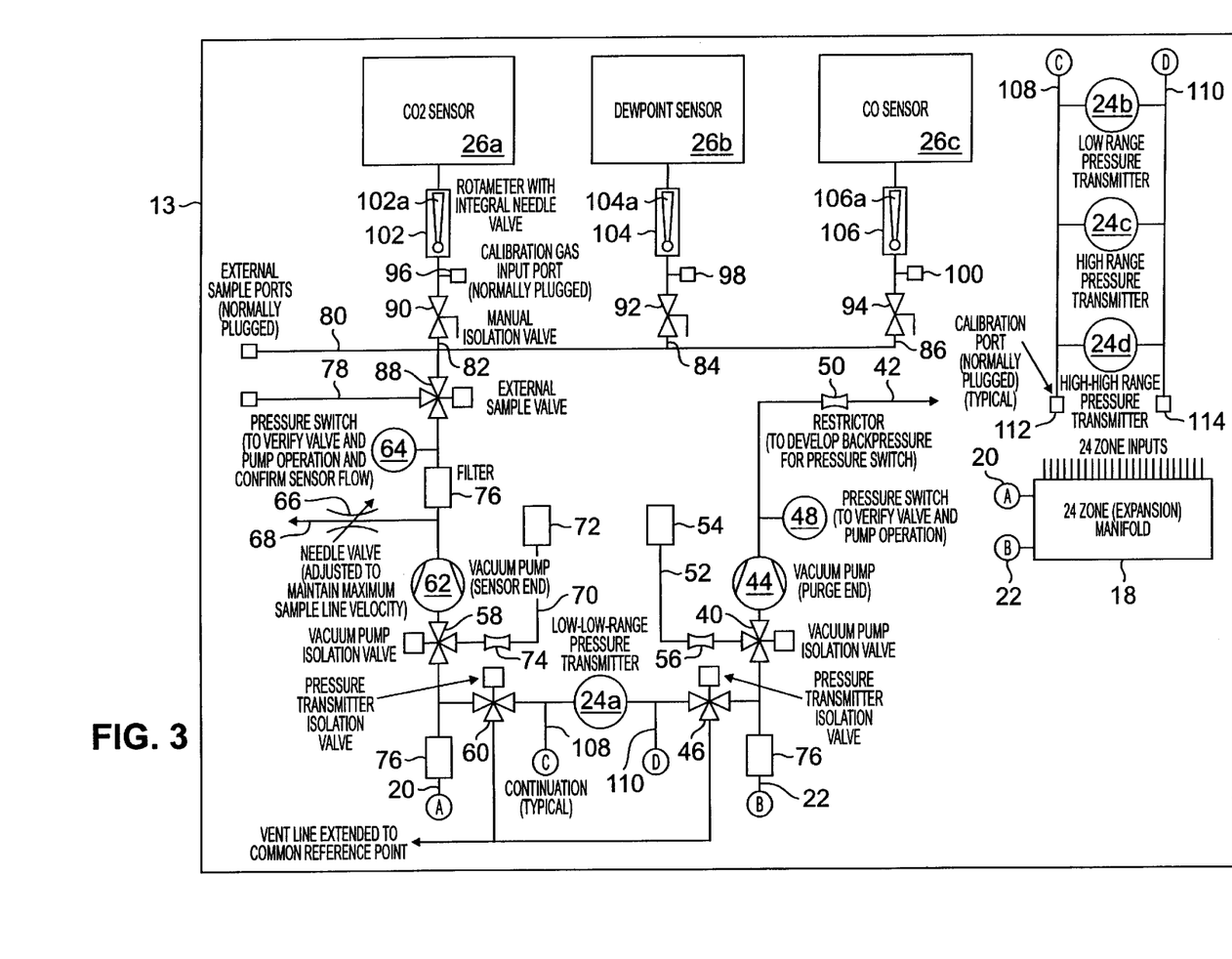
FIG. 3 is a schematic representation of an embodiment of the fluid sampling system of FIG. 2.

FIG. 3 shows an embodiment of a sensor subsystem 13 of the fluid sampling system 14. Fluid samples are drawn into the manifold 18 through the twenty-four input ports and are shunted to either a purge line 22 or a sensor line 20. Typically, before a measurement, the fluid within the manifold 18 and the selected sample tube 16 is purged so that fresh air from the sample zone is sensed. To do this, a vacuum pump isolation valve 40 is positioned by the system controller 36 to couple the purge line 22 to an exhaust port 42, and a purge end vacuum pump 44 is activated. A pressure transmitter isolation valve 46 is positioned by the system controller 36 to decouple the pressure sensors 24a, 24b, 24c, 24d. A pressure switch 48 is activated to ensure that the valve 40 and the vacuum pump 44 are operating correctly. The fluid, e.g., air, is forced through a restrictor 50 that causes a back pressure that ensures the activation of the pressure switch 48. Filtered fluid is supplied to the vacuum pump 44 through a filtration line 52 that connects with the purge line 22 through valve 40. The filtration line 52 includes a filter 54 and a restrictor 56. The supply of fluid through filtration line 52 ensures that the vacuum pump 44 is able to draw an adequate amount of fluid at all times regardless of the amount of fluid flow from the manifold 18 and prevents excess wear on the vacuum pump 44, especially the diaphragm of the pump.

Alternatively, the fluid can be drawn through the sensor line 20. In this mode, the sensor vacuum pump isolation valve 58 is positioned by the system controller 36 to couple the sensors 26a, 26b, 26c to sensor line 20 and a vacuum pump 62 is engaged. A sensor pressure transmitter isolation valve 60 is positioned by the system controller 36 to decouple the pressure sensors 24a, 24b, 24c, 24d and a pressure switch 64 is activated to ensure that the valve 58 and the vacuum pump 62 are operating correctly and to confirm fluid is flowing through the sensors 26a, 26b, 26c. The presence of additional components on the end of sensor line 20 creates a back pressure to activate pressure switch 64. A flow monitor valve 66 is adjusted by the system controller 36 to maintain the velocity of the fluid in the sensor line 20 within tolerable ranges. Specifically, the valve 66 is adjusted manually to exhaust excess fluid from the system 14 through an exhaust port 68 to maintain fluid flow to the sensors 26a, 26b, 26c below maximum allowable levels. Therefore, the excess capacity of the vacuum pump 62 is utilized without damaging the sensors 26. However, the sensors 26a, 26b, 26c are supplied with a constant flow of 500 cc/min when the system is active. Filtered fluid is supplied to the vacuum pump 62 through a filtration line 70 that connects with the sensor line 20. The filtration line 70 includes a filter 72 and a restrictor 74 to ensure the vacuum pump 62 receives adequate fluid flow and, thus, prevents excess wear on the pump.

The fluid sample is filtered by the sensor filter 76 and is shunted to the on-line sensor mechanism 26, shown in FIG. 2. The on-line sensor mechanism 26 is attached to the sensor line 20 such that it is capable of sensing the sample. The on-line sensor mechanism 26 includes five sensor ports 78, 80, 82, 84, 86 and three different sensors 26a, 26b, 26c attached to the sensor line 20: $CO_2$ sensor 26a, dewpoint sensor 26b, and CO sensor 26c. Each of these sensors 26a, 26b, 26c is attached to one of the sensor ports 82, 84, 86. The remaining two ports 78, 80 are external sample ports and normally are plugged, i.e., the flow of fluid is blocked. One of the external sample ports 78 normally is decoupled from the sensor line 20 by an external sample valve 88 operated by the system controller 36.

Each of the three sensors 26a, 26b, 26c can be coupled or decoupled from the sensor line 20 by one of three isolation valves 90, 92, 94, e.g., manually operated or automatically controlled by the system controller 36. Each of the sensors 26a, 26b, 26c also includes a calibration gas port 96, 98, 100 which normally is plugged, and a flowmeter 102, 104, 106, e.g., a rotational flow meter having an integral needle valve (102a, 104a, 106a).

In addition to the sensor data measured by the sensors 26a, 26b, 26c through the sensor line 20, differential pressure can be measured across the sensor and purge lines 20 and 22 by the four pressure sensors 24a, 24b, 24c, 24d. The pressure sensors 24a, 24b, 24c, 24d are in fluid communication with the sensor line 20 via connection line 108 and with the purge line 22 via connection line 110. The ends of the connection lines 108, 110 contain a calibration port 112, 114 that normally is plugged. Differential pressure is measured in a static state with the vacuum pumps 44, 62 disengaged by the system controller 36. The sensor and purge isolation valves 58 and 40 are switched to decouple the sensors 26a, 26b, 26c and the exhaust port 42 from the sensor and pressure lines 20 and 22 and to couple the pressure sensors 24a, 24b, 24c, 24d to the sensor and purge lines 20 and 22. The pressure sensor 26 measurements and the sensor mechanism 24 measurements are not taken at the same time because the sensor mechanism 24 measurements are taken while the system is in a dynamic state. Alternatively, the fluid sampling system 14 could be configured to measure pressure in a dynamic state, e.g., with the vacuum pumps 44 and 62 engaged and fluid moving through the system 14.

Figure 4:
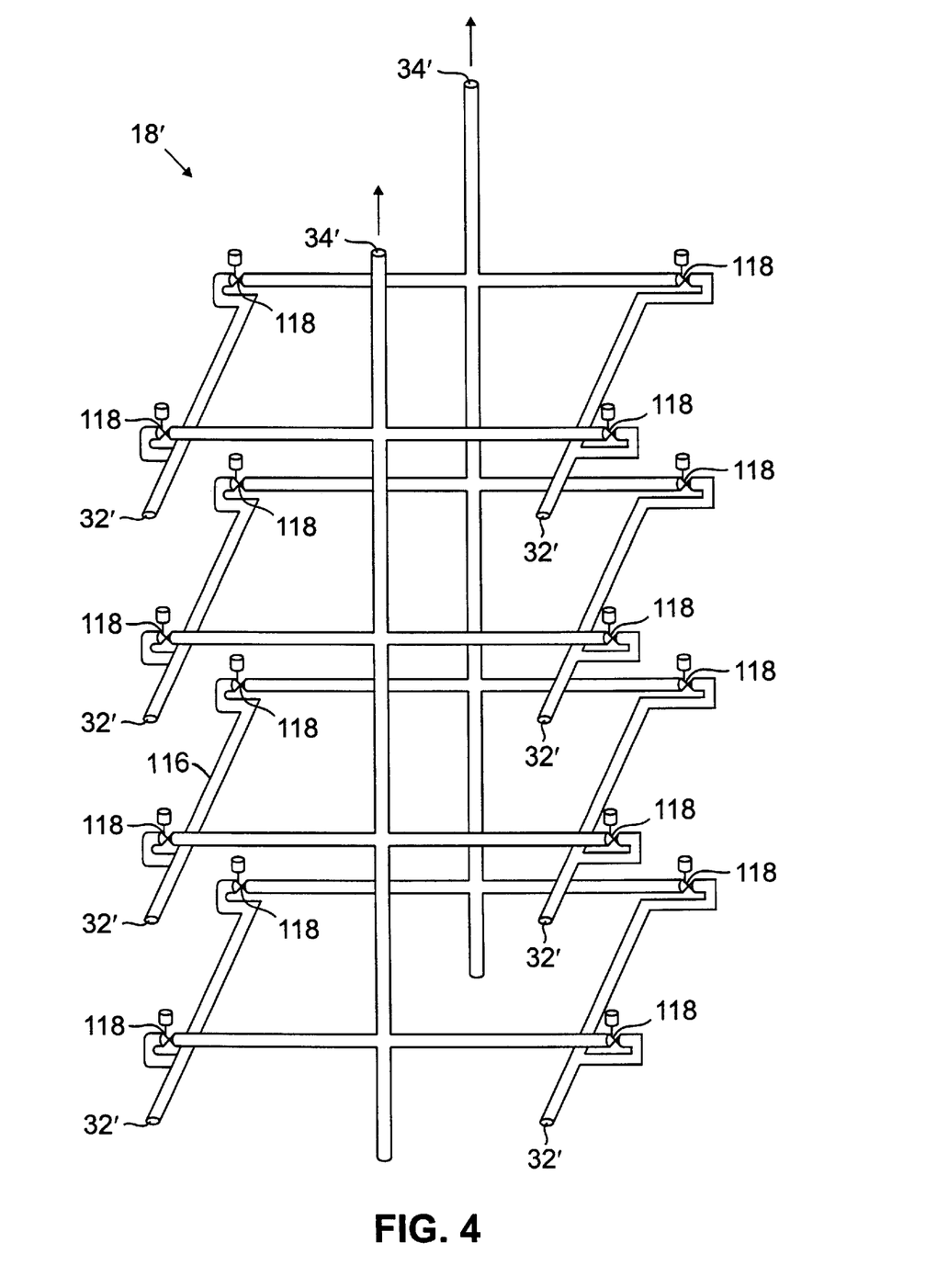
FIG. 4 is a schematic representation of an embodiment of a manifold used in the fluid sampling system of FIG. 2.
Figure 5:
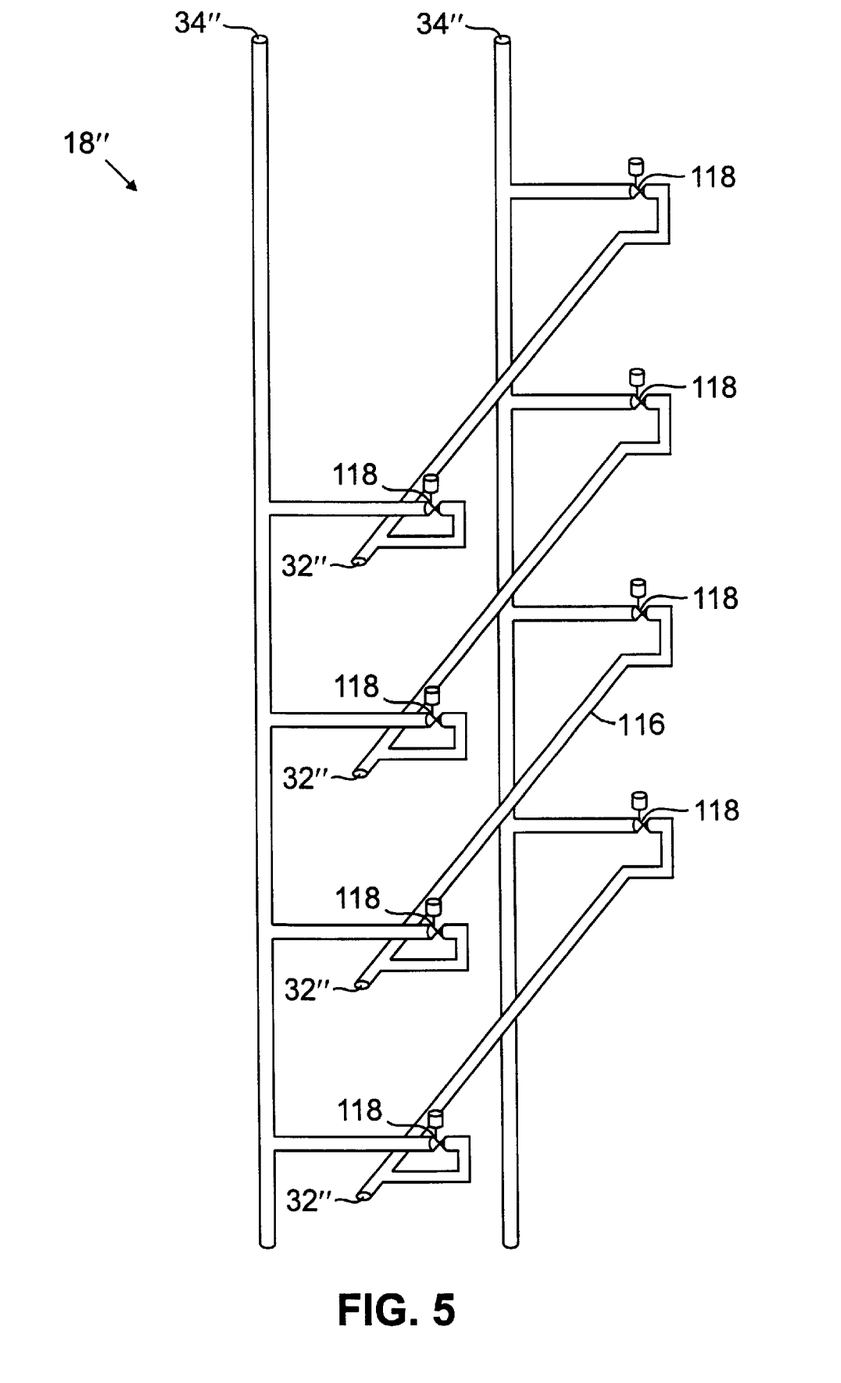
FIG. 5 is a schematic representation of an alternate embodiment of a manifold for the fluid sampling system of FIG. 2.

Referring to FIGS. 4 and 5, the manifold 18', 18" is constructed of, e.g., a metal or a plastic machined or formed to include an arrangement of passages 116 and valves 118 to connect a number of input ports 32', 32" to both the sensor and purge lines 20, 22. A possible material is the machineable plastic Delrin®, an acetal resin manufactured by DuPont. Other materials and combinations are possible. For example, the manifold can be an arrangement of plastic tubes. The manifold 18', 18" has a set of input ports 32', 32" and two output ports 34', 34". Each input port 32', 32" is located at the end of a passage that branches with one branch leading to the output port 34', 34" connected to the sensor line 20 of FIG. 2 and with the other branch leading to the output port 34', 34" connected to the purge line 22 of FIG. 2. A valve 118, e.g., a solenoid valve operated by the system controller 36 is disposed across each branch so that each input port 32', 32" may be coupled and decoupled from each of the output ports 34', 34". Thus, any selected input port or set of input ports 32', 32" can be coupled to either or both of the output ports 34', 34".

In the configuration shown in FIG. 4, there are pairs of input ports 32' aligned along a first plane of the manifold 18' while the two output ports 34' lie at one end of the manifold 18'. In the configuration shown in FIG. 5, a line of unpaired input ports 32" are aligned along a first plane of the manifold 18" while the two output ports 34' lie at one end of the manifold 18". Though either eight or four input ports 32', 32" are depicted in FIGS. 4 and 5 respectively, a manifold 18 having either twelve single or twenty-four paired input ports typically would be used. A manifold 18" with twelve input ports contains twenty-four valves 118. A manifold 18' with twenty-four input ports contains forty-eight valves 118.

Figure 6:
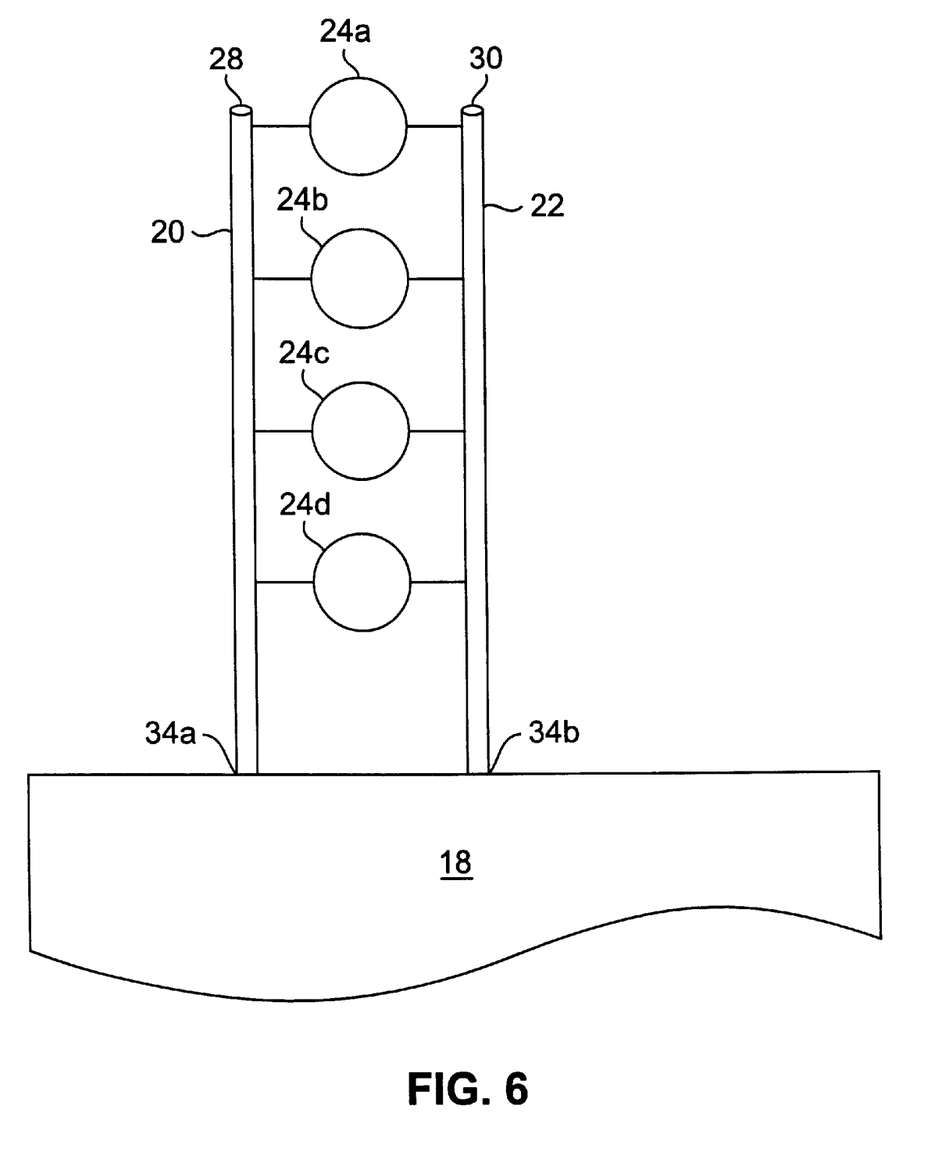
FIG. 6 is a schematic representation of a pressure sensor used in conjunction with the fluid sampling system of FIG. 2.

FIG. 6 shows an embodiment of the differential pressure sensor 24 shown in FIG. 2, and includes four different individual pressure sensors 24a, 24b, 24c, 24d. Each individual sensor 24a, 24b, 24c, 24d is coupled across the sensor line 20 and the purge line 22; the sensor and purge lines 20, 22 are connected respectively to the two output ports 34a and 34b of the manifold. Therefore, each of the pressure sensors 24a, 24b, 24c, 24d is capable of making a differential pressure measurement across any two input ports 32 (shown in FIG. 2) when coupled to the output ports 34a and 34b by the valves 118 (shown in FIGS. 4 and 5) of the manifold 18.

Each of the sensors 24a, 24b, 24c, 24d has a different pressure range in which the sensor is most accurate. The first sensor 24a, which is regarded as a very low pressure sensor, is most accurate in the narrowest range of pressures. The second sensor 24b, which is regarded as a low pressure sensor, is most accurate in a relatively broader range of pressures. The third sensor 24c, which is regarded as a high pressure sensor, is most accurate in a range of pressures that relatively is broader than the first two ranges. The fourth sensor 24d, which is regarded as a very high pressure sensor, is most accurate in a range of pressures that relatively is broader than the other three ranges. The pressure sensors 24a, 24b, 24c, 24d are selected such that the pressure ranges of each individual sensor 24a, 24b, 24c, 24d forms overlapping ranges in which accurate pressure measurements may be taken. Other combinations of sensors, e.g., two, three, or five, could be used.

Figure 7:
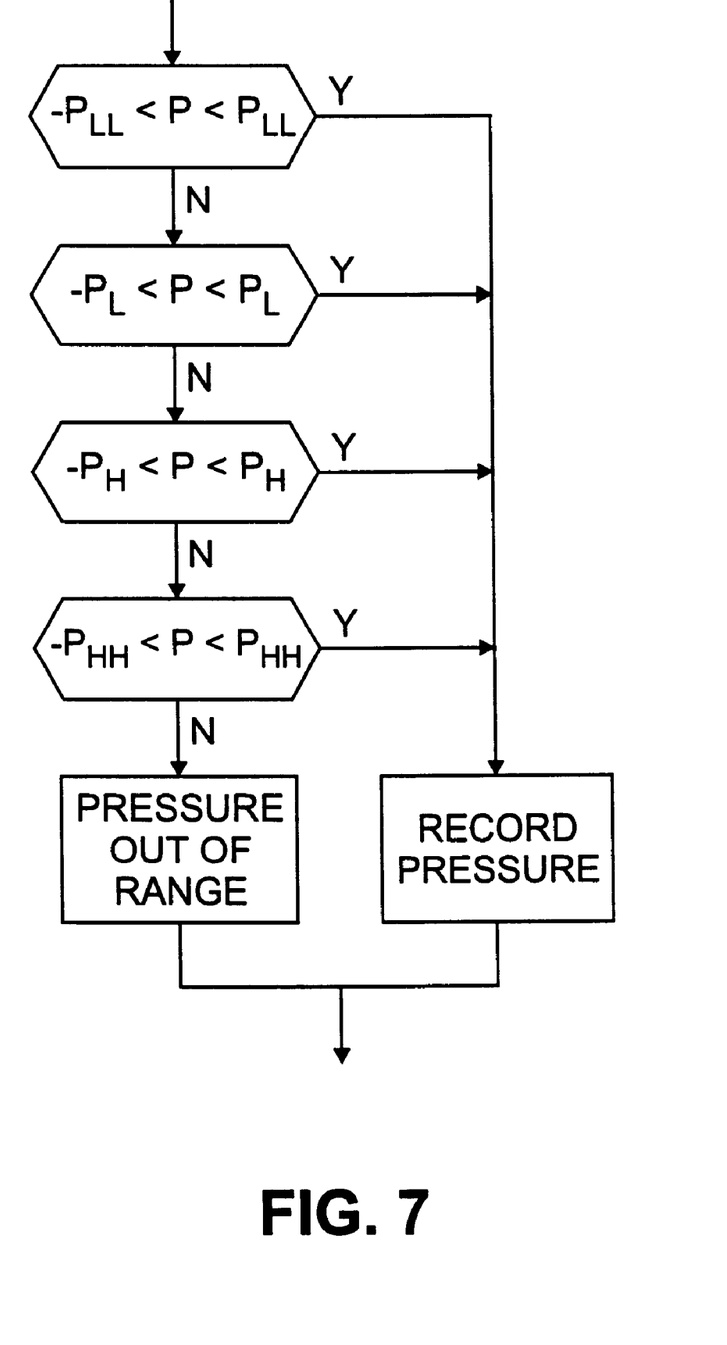
FIG. 7 is a flow chart of the of the measurement logic associated with the pressure sensor of FIG. 6.

The flow chart of FIG. 7 illustrates the logic used to measure, select, and record the pressure across the sensor and purge lines 20, 22. First, the system 14 is brought to a static state by the system controller 36 and the differential pressure sensors 24a, 24b, 24c, 24d measure the differential pressure of the sensor and purge lines 20, 22. The system controller 36, compares the pressure measurements of the individual sensors 24a, 24b, 24c, 24d to the range in which the individual sensors are accurate. The system controller 36 first compares the measurement produced by sensor 24a to the accuracy range of sensor 24a. If sensor 24a produces a pressure measurement in the very low range ($-P_{LL}$–$P_{LL}$), the pressure $P_1$ is recorded as the differential pressure. Similarly, the system controller examines data from each sensor in turn. If sensor 24b produces a pressure measurement in the low range ($-P_L$–$P_L$), the pressure $P_2$ is recorded as the differential pressure. If sensor 24c produces a pressure measurement in the high range ($-P_H$–$P_H$), the pressure $P_3$ is recorded as the differential pressure. If sensor 24d produces a pressure measurement in the very high range ($-P_{HH}$–$P_{HH}$), the pressure $P_4$ is recorded as the differential pressure. If none of the pressure measurements are within the range of the associated sensors 24a, 24b, 24c, 24d, then the system controller 36 records an error message that the differential pressure is out of range. As an example, the ranges sensors 24a, 24b, 24c, and 24d are bi-directional sensors with ranges, respectively, of 0 to +/–0.10" $H_2O$, 0 to +/–0.25" $H_2O$, 0 to +/–1.0" $H_2O$, and 0 to +/–5.0" $H_2O$. The accuracy of the sensors 24a, 24b, 24c, and 24d is +/–2%.

Figure 8:
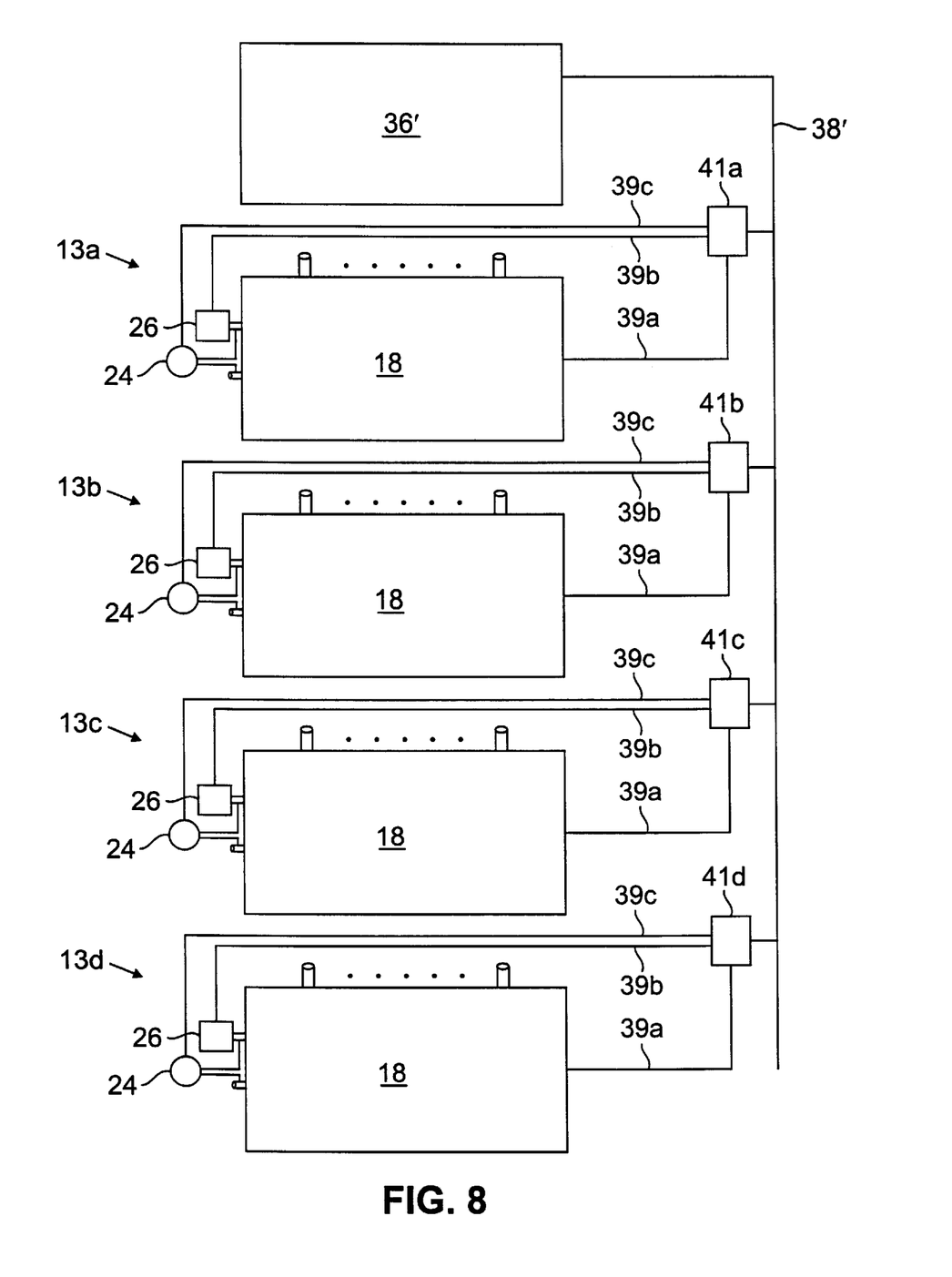
FIG. 8 is an embodiment of the fluid sampling system of FIG. 2.

FIG. 8 shows an alternate embodiment of the fluid sampling system 14 shown in FIG. 2 that includes a system controller 36' connected to multiple manifolds 18 (here four manifolds being shown). The single system controller 36' controls the entire system rather than one system controller 36 controlling each manifold. Typically the manifolds 18 would have either twelve or twenty-four input ports and two output ports. The system controller 36' sends signals to control all of the elements of subsystem 13 shown in FIG. 3, e.g., the valves 118 of the manifold and the automatic valves 46 and 60 of lines 20 and 22, the sensors 26, the differential sensors 24, the vacuum sources 44 and 62, the pressure switches 48 and 64, and any additional elements of an alternate embodiment of the system that are actuated automatically.

As shown, the sensor subsystems 13a–d are connected to the system controller 36' via respective network interfaces 41a–d. The interfaces 41a–d send signals from the controller 36' to the manifold 18, the sensor bank 26, the differential pressure bank 24 via respective connections 39a, 39b, and 39c. The interfaces 41a–d are connected to the system controller via connection 38.

Other Embodiments

It is to be understood that while the invention has been described in conjunction with the detailed description thereof, the foregoing descriptions are intended to illustrate and not limit the scope of the invention, which is defined by the scope of the appended claims. Other aspects, advantages, and modifications are within the scope of the appended claims.

For example, the manifold can have more than two output lines, a different number of input ports, or a different coupling arrangement, e.g., some, but not all input ports coupled to all output ports. A second sensor line can be connected to an additional output port to measure differential temperature or other measurements. The fluid sampling system can include more, fewer, or different sensor arrangements as well as a different arrangement of components to actuate the system. The sampled fluid can be gases other than air such as the exhaust gases of a landfill, or the sampled fluid can be liquids such as water and oil.

What is claimed is:

1. A fluid sampling device comprising:

a manifold having a plurality of inputs, a common purge pathway and a common sampling pathway;

a plurality of valves disposed to couple and decouple all, a subset, or none of the inputs to the common purge pathway, and all, a subset, or none of the inputs to the common sampling pathway; and a sensor coupled to the common purge or common sampling pathway, or a differential sensor coupled to the common purge and common sampling pathways.

2. The fluid sampling device of claim 1, further comprising a controller connected to the plurality of valves, the controller producing control signals that enable the valves to couple and decouple the inputs to the common sampling and purge pathways.

3. The fluid sampling device of claim 2, wherein the controller produces the control signals to configure the valves such that a first valve of the plurality couples a first input to the common sampling pathway, a second valve of the plurality couples a second input to the common purge pathway, and a set of valves decouples the common sampling and purge pathways from other inputs.

4. The fluid sampling device of claim 2, wherein the controller produces the control signals to cause the differential sensor to measure differential pressure across the common sampling pathway and the common purge pathway.

5. The fluid sampling device of claim 2, wherein the differential sensor comprises a first pressure sensor coupled to the common sampling pathway and a second pressure sensor coupled to the common purge pathway.

6. The fluid sampling device of claim 2, wherein the differential sensor comprises a plurality of differential pressure sensors.

7. The fluid sampling device of claim 6, wherein a first sensor of the plurality measures pressure within a different range than a second sensor of the plurality.

8. The fluid sampling device of claim 6, wherein the controller causes first and second differential pressure sensors to each measure differential pressure across the common sampling pathway and the common purge pathway to provide first and second indications of the differential pressure between the first and second input ports.

9. The fluid sampling device of claim 8, wherein the controller causes one of the first and second indications to provide a measurement from the sampling device based on the value of the first and second indications and pressure ranges for each of the first and the second sensors.

10. A fluid sampling device comprising:

a manifold having a plurality of input ports, a first common output port, and a second common output port;

a plurality of paired valves, each pair of valves of the plurality corresponding to an input port of the plurality of input ports, each first valve of each pair disposed to couple and decouple the input port to the first common output port, each second valve of the pair disposed to couple and decouple the input port to the second common output port; and a differential pressure sensor coupled to the common output ports.

11. The fluid sampling device of claim 10, further comprising:

a controller connected to the plurality of paired valves, the controller producing control signals that actuate the first and second valves.

12. The fluid sampling device of claim 11, wherein the controller produces the control signals to configure the valves such that a first valve of the plurality couples a first input to the first common output port, a second valve of the plurality couples a second input to the second common output port, and a set of the valves decouples the first and second common output ports from other input ports.

13. The fluid sampling device of claim 12, wherein the controller produces the control signals to cause the differential pressure sensor to measure differential pressure across the first and second common output ports.

14. The fluid sampling device of claim 11, wherein the differential pressure sensor comprises a first pressure sensor coupled to the first common output port and a second pressure sensor coupled to the second common output port.

15. The fluid sampling device of claim 11, wherein the differential pressure sensor comprises a plurality of pressure sensors.

16. The fluid sampling device of claim 15, wherein a first pressure sensor of the plurality measures pressure within a different range than a second pressure sensor of the plurality.

17. The fluid sampling device of claim 14, wherein the controller causes the first and the second pressure sensors to each measure differential pressure across the first and second common output ports to provide first and second indications of the differential pressure between the first and second input ports.

18. The fluid sampling device of claim 17, wherein the controller causes one of the first and second indications to provide a measurement from the sampling device based on the value of the first and second indications and pressure ranges for each of the first and the second pressure sensors.

19. A fluid sampling device comprising:

a manifold comprising a first common pathway, a second common pathway, and a first input port, the manifold having a plurality of passages, the first input port being in fluid communication with the first common pathway through one of the plurality of passages;

a first valve disposed along the passage capable of blocking the flow of fluid between the input port and the first common pathway;

a second valve disposed along a second of the plurality of passages able to block the flow of fluid between the input pert and the second common pathway; and a differential sensor disposed across the first common pathway and the second common pathway.

20. The fluid sampling device of claim 19, further comprising:

a second input port in fluid communication with the first common pathway through a third of the plurality of passages and in fluid communication with the second common pathway through a fourth of the plurality of passages;

a third valve disposed along the third passage; and a fourth valve disposed along the fourth passage, wherein the third valve and the fourth valve are capable of blocking the flow of fluid between the second input port and the first and second common pathways, respectively.

21. The fluid sampling device of claim 19, further comprising a controller connected to the valve, wherein the controller is capable of producing control signals that enable the valve to couple and decouple the input port to the first common pathway.

22. The fluid sampling device of claim 20, further comprising a controller connected to the first, second, third and fourth valves, the controller producing control signals to configure the valves such that the first valve couples the first input port to the first common pathway, the fourth valve couples the second input port to the second common pathway, the second valve decouples the first input port from the second common pathway, and the third valve decouples the second input port from the first common pathway.

23. The fluid sampling device of claim 20, further comprising a controller connected to the first, second, third, and fourth valves, wherein the controller is capable of producing control signals to configure the valves such that the second valve couples the first input port to the second common pathway, the third valve couples the second input port to the first common pathway, the first valve decouples the first input port from the first common pathway, and the fourth valve decouples the second input port from the second common pathway.

24. The fluid sampling device of claim 23, wherein the controller produces the control signals to cause the differential sensor to measure differential pressure across the first and second common pathways.

25. The fluid sampling device of claim 20, wherein the differential sensor comprises a plurality of pressure sensors.

26. The fluid sampling device of claim 22, wherein the differential sensor comprises a first pressure sensor coupled to the first common pathway and a second pressure sensor coupled to the second common pathway.

27. The fluid sampling device of claim 26, wherein the controller causes the first and the second pressure sensors to each measure differential pressure across the first and second common pathways to provide first and second indications of the differential pressure between the first and second input ports.

28. The fluid sampling device of claim 27, wherein the controller causes one of the first and second indications to provide a measurement from the sampling device based on the value of the first and second indications and pressure ranges for each of the first and the second pressure sensors.

29. A fluid sampling device comprising:
a manifold comprising a first input port and a first output port, the first input port being in fluid communication with the first output port through a first passage;
a first valve disposed along the first passage, the first valve having a coupling and decoupling position;
a pressure sensor connected to the first output port; and
a controller producing control signals that enable the first valve to couple and decouple the first input and the first output port.

30. The fluid sampling device of claim 29, further comprising a second input port and a second output port, the second input port being in fluid communication with the second output port through a second passage, the controller producing control signals that enable a second valve to couple and decouple the second input port and the second output port, the pressure sensor further connected to the second output port.

31. The fluid sampling device of claim 30, wherein the controller produces the control signals to configure the valves such that the first valve couples the first input port to the first output port and the second valve couples the second input to the second output port.

32. The fluid sampling device of claim 31, wherein the controller produces the control signals to cause the pressure sensor to measure differential pressure across the first and second output ports.

33. The fluid sampling device of claim 31, wherein the pressure sensor is a plurality of pressure sensors.

34. The fluid sampling device of claim 33, wherein the controller causes a first and a second pressure sensors of the plurality to each measure differential pressure across the first and second output ports to provide first and second indications of the differential pressure between the first and second input ports.

35. The fluid sampling device of claim 34, wherein the controller causes one of the first and second indications to provide a measurement from the sampling device based on the value of the first and second indications and pressure ranges for each of the first and the second pressure sensors.

36. The fluid sampling device of claim 29, wherein the manifold comprises a plurality of input and output ports, a common purge pathway, a common sampling pathway, and a plurality of valves disposed to couple and decouple all, a subset, or none of the inputs to the common purge pathway, and all, a subset, or none of the inputs to the common sampling pathway.

37. A fluid sampling system comprising:
a manifold comprising first and second output pathways, first and second input ports, and a plurality of passages, wherein the first input port is in fluid communication with the first output pathway through a first of the plurality of passages, and the second input port is in fluid communication with the second output pathway through a second of the passages of the plurality of passages;
a plurality of valves having a coupled and a decoupled position, wherein one valve of the plurality of valves is disposed along the first passage;
a differential pressure sensor disposed across the first and second output pathways;
a sample zone,
a sample tube disposed to establish fluid communication between the sample zone and the first or second input port;
a sensor connected to the first or second output pathway; and
a system controller connected to the manifold.

38. The fluid sampling device of claim 37, wherein the system controller configures the valves such that the one valve couples the first input port to the first output pathway, and such that a second valve couples the second input port to the second output pathway.

39. The fluid sampling device of claim 38, wherein the controller produces control signals to cause the differential pressure sensor to measure differential pressure across the first and second output pathways.

40. The fluid sampling device of claim 38, wherein the differential pressure sensor comprises a plurality of pressure sensors.

41. The fluid sampling device of claim 40, wherein the controller causes first and second pressure sensors of the plurality of sensors to each measure differential pressure across the first and second output pathways to provide first and second indications of the differential pressure between the first and second input ports.

42. The fluid sampling device of claim 41, wherein the controller causes one of the first and second indications to provide a measurement from the sampling device based on the value of the first and second indications and pressure ranges for each of the first and the second pressure sensors.

* * * * *